United States Patent
Wei

(10) Patent No.: US 7,280,221 B2
(45) Date of Patent: Oct. 9, 2007

(54) HIGH EFFICIENCY LOW COHERENCE INTERFEROMETRY

(75) Inventor: Jay Wei, Fremont, CA (US)

(73) Assignee: Optovue, Inc., Fremont, CA (US)

( * ) Notice: Subject to any disclaimer, the term of this patent is extended or adjusted under 35 U.S.C. 154(b) by 312 days.

(21) Appl. No.: 11/055,900

(22) Filed: Feb. 10, 2005

(65) Prior Publication Data

US 2005/0174578 A1 Aug. 11, 2005

Related U.S. Application Data

(60) Provisional application No. 60/543,767, filed on Feb. 10, 2004.

(51) Int. Cl.
*G01B 9/02* (2006.01)
(52) U.S. Cl. ............. 356/479; 356/477; 356/495; 356/497
(58) Field of Classification Search ............ 356/479, 356/489, 495, 496, 497, 511, 512, 477
See application file for complete search history.

(56) References Cited

U.S. PATENT DOCUMENTS

| | | | |
|---|---|---|---|
| 3,767,307 A * | 10/1973 | Bowker | 356/489 |
| 5,202,745 A | 4/1993 | Sorin et al. | |
| 5,321,501 A | 6/1994 | Swanson et al. | |
| 5,371,588 A * | 12/1994 | Davis et al. | 356/489 |
| 5,537,162 A | 7/1996 | Hellmuth et al. | |
| 5,894,531 A * | 4/1999 | Alcoz | 385/11 |
| 6,053,613 A | 4/2000 | Wei et al. | |
| 6,252,666 B1 * | 6/2001 | Mandella et al. | 356/479 |
| 6,325,512 B1 | 12/2001 | Wei | |
| 6,385,358 B1 * | 5/2002 | Everett et al. | 385/12 |
| 6,501,551 B1 | 12/2002 | Tearney et al. | |

(Continued)

FOREIGN PATENT DOCUMENTS

DE 198 57 001 A1 6/2000

(Continued)

OTHER PUBLICATIONS

Andrew M. Rollins and Joseph A. Izatt, "Optimal interferometer designs for optical coherence tomography," Optics Letters, vol. 24, No. 21, Nov. 1, 1999, pp. 1484-1486.*

(Continued)

*Primary Examiner*—Gregory J. Toatley, Jr.
*Assistant Examiner*—Scott M Richey
(74) *Attorney, Agent, or Firm*—Finnegan, Henderson, Farabow, Garrett & Dunner, L.L.P.

(57) ABSTRACT

In accordance with the present invention, embodiments of interferometers are presented that improves both the polarization dependency problem and helps prevents light from being reflected back into the light source, among other things. Interferometer embodiments can include an isolator coupled to a light source and polarization dependent optics coupled with the isolator to provide light to a reference arm and a sample arm, wherein reflected light provided to optical detectors is such that a polarization independent optical signal can be formed in an optical signal processor coupled to the optical detectors, and the isolator blocks reflected light from the reference arm and the sample arm from entering the light source. In some embodiments, a balanced detection system can be utilized to reduce noise.

6 Claims, 14 Drawing Sheets

U.S. PATENT DOCUMENTS

| | | | |
|---|---|---|---|
| 6,575,573 B2 | 6/2003 | Lai et al. | |
| 6,822,741 B2 * | 11/2004 | Aronkyto et al. | 356/417 |
| 7,046,371 B2 * | 5/2006 | De Lega et al. | 356/511 |
| 7,102,756 B2 * | 9/2006 | Izatt et al. | 356/479 |
| 2003/0011745 A1 | 1/2003 | Molebny et al. | |
| 2003/0028100 A1 | 2/2003 | Tearney et al. | |
| 2005/0140982 A1 * | 6/2005 | Chen et al. | 356/479 |
| 2005/0203422 A1 | 9/2005 | Wei | |

FOREIGN PATENT DOCUMENTS

| | | |
|---|---|---|
| EP | 0 697 611 A2 | 2/1996 |
| WO | WO 00/28884 | 5/2000 |
| WO | WO 03/105678 A2 | 12/2003 |

OTHER PUBLICATIONS

Michael R. Hee and David Huang, Eric A. Swanson, James G. Fujimoto, "Polarization-sensitive low-coherence reflectometer for birefringence characterization and ranging," Journal of the Optical Society of America B, vol. 9, No. 6, Jun. 1992, pp. 903-908.*

International Search Report and Written Opinion from related PCT Application No. PCT/US2005/003871 filed Feb. 9, 2005.

Izatt, J. et al., "Micrometer-Scale Resolution Imaging of the Anterior Eye in Vivo With Optical Coherence Tomography," Arch Ophthalmol (1994), vol. 112, pp. 1584-1589.

U.S. Appl. No. 11/056,537, filed Feb. 10, 2005.

Danielson, B.L. et al., "Guided-Wave Reflectometry with Micrometer Resolution," Applied Optics (1987), vol. 26, No. 14, pp. 2836-2842.

Golubovic, B. et al., "Optical Frequency-Domain Reflectometry Using Rapid Wavelength Tuning of a $Cr^{4+}$:Forsterite Laser," Optical Society of America (1997), vol. 22, No. 22, pp. 1704-1706.

Haigis, W. et al., "Comparison of Immersion Ultrasound Biometry and Partial Coherence Interferometry for Introcular Lens Calculation According to Haigis," Graefe's Arch Clin Exp Ophthalmol (2000) 238: 765-773.

Hamed et al., "A Comparative Analysis of Five Methods of Determining Corneal Refractive Power in Eyes that have Undergone Myopic Laser in Situ Keratomileusis," American Academy of Ophthalmology (2000), vol. 109, No. 4, pp. 651-658.

Hee, M. et al., "Polarization-Sensitive Low-Coherence Reflectometer for Birefringence Characterization and Ranging," Opitcal Society of America (1992), vol. 9, No. 6, pp. 903-908.

Hitzenberger, C.K. et al., "Measurement of the Axial Eye Length and Retinal Thickness by Laser Doppler Interferometry (LDI)," Ophthalmic Technologies (1991), vol. 1423, pp. 46-50.

Huang, D. et al., "Opitcal Coherence Tomography," Science (1991), vol. 254, pp. 1178-1181.

Kobayashi, M. et al., "Polarization-Independent Interferometric Optical-Time-Domain Reflectometer," IEEE (1991), vol. 9, No. 5, 6 pages.

Park, H. et al., "High Resolution Optical Ranging System," Applied Optics (1981), vol. 20, No. 14, pp. 2389-2394.

Preussner, P.R., "Ray Tracing for Intraocular Lens Calculation," Elsvier Science Inc. (2001), vol. 28, pp. 1412-1419.

Radhakrishnam, S. et al., "Real-Time Optical Coherence Tomography of the Anterior Segment at 1310 nm," American Medical Association (2001), vol. 119, pp. 1179-1185.

Rollins, A. et al., "Optimal Interferometer Designs for Optical Coherence Tomography," Optical Society of America (1999), vol. 24, No. 21, pp. 1-3.

Sorin, W.V. et al., "Simultaneous Thickness and Group index Measurement Using Opitcal Low-Coherence Reflectometry," IEEE (1992), vol. 4, No. 1, pp. 105-107.

Takada, K. et al., "New Measurement System for Fault Location in Optical Waveguide Devices Baded on an Interferometric Technique," Applied Optics (1987), vol. 26, vol. 9, pp. 1603-1606.

Non-final Office Action mailed Apr. 4, 2007, for U.S. Appl. No. 11/056,537, filed Feb. 10, 2005.

* cited by examiner

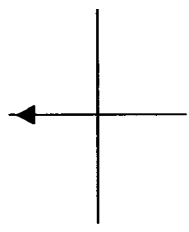
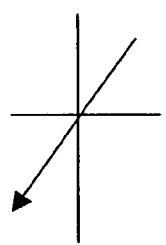
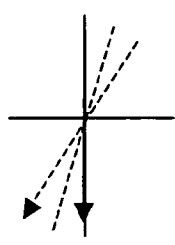
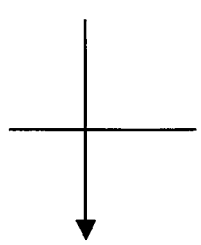
FIG. 5B   FIG. 5C   FIG. 5D   FIG. 5E
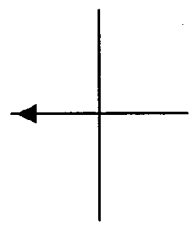
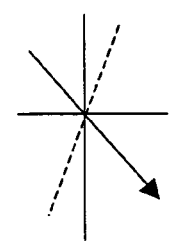
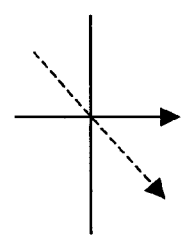
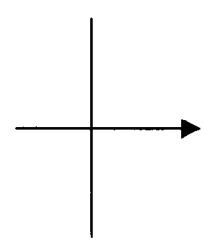
FIG. 5F   FIG. 5G   FIG. 5H   FIG. 5I

HIGH EFFICIENCY LOW COHERENCE INTERFEROMETRY

RELATED APPLICATIONS

The present application claims priority to Provisional Application No. 60/543,767, "High Efficiency Low Coherence Interferometry," by Jay Wei, filed on Feb. 10, 2004, which is herein incorporated by reference in its entirety.

BACKGROUND

1. Field of the Invention

The present invention relates to interferometry and, in particular, to high efficiency interferometers that can be employed in non-invasive optical imaging and measuring devices such as optical coherence tomography and optical coherence reflectometry.

2. Discussion of Related Art

Low coherence interferometry, which derives from classical white light interferometer, has received increasing scrutiny over the last decade or so for its application to optical coherence reflectometry and optical coherence tomography. Optical coherence reflectometry and optical coherence tomography are both techniques for mapping images of eyes and can be highly beneficial for diagnosing and curing defects in eyes. Further, low coherence interferometry can be utilized in endoscopy, laparoscopy, microscopy, and any other technique where interferometric techniques may be useful.

FIG. 1 illustrates an example of a conventional low coherence interferometer 100. Low coherence interferometer 100, as shown in FIG. 1, is a simple Michaelson interferometer that includes a light source 101, a beam splitter 102, and an optical signal processing unit 110. As shown in FIG. 1, beamsplitter 102 can be a 2×2 beamsplitter that splits a low coherence light beam from light source 101 received from source arm 103 into a reference beam coupled into reference arm 104 and a sample beam coupled into sample arm 105. The reference beam on reference arm 104 is reflected back to beam splitter 102 by reference 112, and the sample beam on sample arm 105 is reflected back to beam splitter 102 by sample 111. Beam splitter 102 splits the reflected reference beam into source arm 103 and signal arm 106. Similarly, beam splitter 102 splits the reflected beam from sample 111 into both source arm 103 and signal arm 106. The reflected light beam from sample 111 and from reference 112 are, therefore, combined into a combined beam coupled into source arm 103 by beam splitter 102. The signal beam in signal arm 106 is received by a photodetector and a transmittance amplifier TIA 107, where the optical signal is converted to an electronic signal. The electronic signal is coupled into optical signal processing unit 110 for further processing. The function of the optical signal processing undertaken in optical signal processing 110 can include bandpass filtering, signal amplification, demodulation, lowpass filtering and other processing functions. The optical signals obtained at optical signal processing unit 110 can be processed either through hardware or software for imaging and analyzing the structure and optical properties of sample 111 (the sample under test).

An example of an optical coherence domain reflectometer based on the Michaelson interferometer as shown in FIG. 1 has been discussed by Youngquist & Davis in Optics Letter 12, 158-160, March 1987. An optical reflectometry with a transverse scan mechanism for tomographic imaging has been described by Park in Applied Optics 1987. Optical coherence tomography for imaging bio-tissue based on interferometry for bio-tissue image is also discussed in U.S. Pat. No. 5,321,501.

In the example of the Michaelson interferometer shown in FIG. 1, portions of the reflected signal from sample arm 105 and reference arm 104 also propagate into source arm 103. This is disadvantageous for optical performance. First, useful signal is lost to source arm 103. Second, the reflected light in source arm 103 will increase the noise on the light beam generated by light source 101.

A solution to reflected light into source arm 103 is described in Rollin's paper in Optics Letters Vol 24, No. 21, November 1999. As shown in FIG. 2, an optical circulator 202 is inserted in source arm 103 of interferometer 200. Beam path 203 is optically coupled between beam splitter 102 and circulator 202. As shown in FIG. 2, light reflected down beam path 203 from beam splitter 102 enters circulator 202 and is routed to detector 207 through beam path 205. The output signals from detectors 107 and 207 are combined in differential amplifier 208 and then input to optical signal processing unit 110. Such an arrangement serves two purposes: First, the reflected beams are routed into detector beam path 205 and 106; and second, circulator 202 also functions as an isolator to keep reflected light away from light source 101.

Another method is disclosed in U.S. Pat. No. 6,501,551. In the solution described in the '551 patent, both sample arm 105 and reference arm 104 include an optical circulator. The reflected signal from sample 111 and reference 112 are then routed to another beamsplitter that is different from beamsplitter 102. The two output signals of the new beamsplitter can be individually received, demodulated, and processed before one channel is subtracted from the other in a balanced detection receiver.

However, the signal strength measured at detector 107 is also sensitive to the polarization state of the light beam reflected from sample 111. It is particularly disadvantageous when the sample material of sample 111 is highly birefringent. FIG. 3 illustrates an example interferometer system 300, as disclosed by Sorin in U.S. Pat. No. 5,202,745. Interferometer system 300 can be independent of the polarization state of the sample beam reflected from sample 111 because detector arm 106 can be optically coupled to a polarization diversity receiver. As shown in FIG. 3, the polarization diversity receiver can include polarization beamsplitter 305 coupled to optical detectors 310 and 311 by transmission arms 306 and 307, respectively. As shown in FIG. 3, light source 101 is first linear polarized by coupling light from source arm 103 into a linear polarizer 302. Polarization beamsplitter (PBS) 305 is placed in the detector arm 106 to split the beam into two orthogonally polarized beam paths 306 and 307. A polarization controller 308 can also be coupled into reference arm 104 and adjusted to produce equal reference signal power in each of polarization arms 306 and 307 of the polarization diversity receiver. These two polarization arm signals are individually demodulated and processed before being summed in optical signal processing unit 110. In the example interferometer system 300, no matter what the polarization state of the refelected beam in sample arm 105, the reflected beam from sample arm 105 will eventually interfere with its own properly polarized reference beam and the resulting beam will be summed. The signal is constant with respect to the changes of the polarization state of the sample beam.

However, neither of the systems illustrated in FIGS. 2 and 3 solve both the polarization problem and the problem of light reflected back into the light source. In light of above mentioned disadvantages of the prior art and other shortcomings, there is a need to resolve both polarization and light reflected into source arm issues in a single interferometer, as it is desirable to maximum the signal, consistent with a change of polarization due to the sample, to the detectors as well as to reduce the noise level from the light source.

SUMMARY

In accordance with the present invention, embodiments of an interferometer that solves both the polarization and the reflected light issues are presented. An interferometer according to embodiments of the present invention can include a light source; an isolator coupled to the light source; polarization dependent optics coupled to the isolator; a reference arm coupled to the polarization dependent optics; a sample arm coupled to the polarization dependent optics; and one or more optical detectors coupled to the polarization dependent optics, wherein the polarization dependent optics couples light into the reference arm and the sample arm, receives reflected light from the reference arm and the sample arm, and provides light to the detectors such that a polarization independent optical signal can be formed in an optical signal processor coupled to the one or more optical detectors, and wherein the isolator blocks reflected light from the reference arm and the sample arm from entering the light source.

In some embodiments of the invention, the isolator can include a circulator coupled to receive light from the light source in a first port. In some embodiments, the polarization dependent optics can include a polarization dependent beam splitter coupled to receive light from a second port of the circulator, the polarization beam splitter providing light of a first polarization, receiving light reflected from the sample arm and the reference arm, and providing light to a first detector of the one or more optical detectors and to the second port of the circulator depending on polarization; a beam splitter coupled to receive the light of the first polarization from the polarization beam splitter, the beam splitter coupling the light of the first polarization into the reference arm and the sample arm and coupling reflected light from the reference arm and the sample arm back into the polarization dependent beam splitter, wherein the circulator provides light to a second detector of the one or more optical detectors through a third port.

In some embodiments, the isolator includes a beam splitter, the beam splitter receiving light from a light source and providing a first beam at a first polarization and a second beam at a second polarization. In some embodiments, the polarization dependent optics includes a Faraday rotator coupled to receive the first beam and the second beam; a wave plate coupled to the Faraday rotator, wherein the polarization of the first beam is rotated into the second polarization and the polarization of the second beam is rotated into the first polarization; a prism coupled to receive the first beam and the second beam from the wave plate and combine the first beam with the second beam; and a beam splitter coupled to the prism, the beam splitter providing light to the reference arm and the sample arm and receiving reflected light from the reference arm and the sample arm, wherein, the reflected light is split by polarization in the prism, the polarization is rotated by the wave plate and the Faraday rotator, and the beam splitter recombines the beams and couples a combined beam to a second polarization beam splitter, and wherein the second polarization beam splitter separates the beam according to polarization and is coupled to the one or more optical detectors. In some embodiments, a power monitor coupled to receive reflected light from the beam splitter can be included.

In some embodiments, the isolator can include a first circulator coupled into the reference arm; and a second circulator coupled into the sample arm. In some embodiments, the polarization dependent optics can include a linear polarizer coupled to receive and polarize light from the light source; a first beam splitter coupled to receive the polarized light from the linear polarizer and provide a light beam to a first port of the first circulator in the reference arm and a first port of the second circulator in the sample arm, wherein the second port of the first circulator is coupled to a reference and the second port of the second circulator is coupled to a sample; a second beam splitter coupled to receive light from a third port of the first circulator and a third port of the second circulator and to provide a combined beam; and a polarization dependent beam splitter coupled to receive the combined beam and provide a first beam of a first polarization and a second beam of a second polarization to the one or more optical detectors. In some embodiments, a power monitor coupled to the second beam splitter.

In some embodiments, the isolator can include a polarization dependent beam splitter, the polarization dependent beam splitter coupled to receive light from the light source and provide a beam of a first polarization. In some embodiments, the polarization dependent optics can include a Faraday rotator and a wave plate coupled to receive the beam of the first polarization and output the beam of the first polarization; a second polarization beam splitter coupled to receive the beam of the first polarization from the Faraday rotator and the wave plate and transmit the beam of the first polarization; and a beam splitter coupled to receive the beam of the first polarization from the second polarization beam splitter, couple the beam of the first polarization in the sample arm and the reference arm, receive a reflected beam from the sample arm and the reference arm, and combine the reflected beams from the sample arm and the reference arm into a combined reflected beam, wherein, the combined reflected beam is separated into a combined reflected beam of the first polarization and a combined reflected beam of a second polarization by the second polarization beam splitter, the combined reflected beam of the second polarization being coupled to one of the one or more optical detectors, and wherein the combined reflected beam of the first polarization is polarization rotated to the second polarization by the Faraday rotator and the wave plate and coupled into another of the one or more optical detectors by the polarization beam splitter. In some embodiments, a power monitor can be coupled to the beam splitter.

In some embodiments, where the isolator is a polarization dependent beam splitter, the polarization dependent optics can include a Faraday rotator and wave plate coupled to receive the first beam of the first polarization and rotate the polarization to a second polarization; a second prism coupled to receive the beam of the second polarization from the Faraday rotator and wave plate; a beam splitter coupled to receive the beam of the second polarization from the second prism, couple light into the reference arm and the sample arm, receive a reflected beam from the sample arm the reference arm, and provide a combined reflected beam, wherein the combined reflected beam is separated by polarization in the second prism into a first reflected beam of the first polarization and a second reflected beam of the second polarization, wherein the Faraday rotator and wave plate rotates the polarization of the second reflected beam of the second polarization into the first polarization, and wherein the polarization dependent beam splitter couples the second reflected beam into the one or more optical detectors. In some embodiments, a power monitor can be coupled to the beam splitter.

In some embodiments the polarization dependent optics can include a Faraday rotator and wave plate coupled to receive the first beam of the first polarization and transmit the first beam of the first polarization; a second prism coupled to receive the first beam of the first polarization from the Faraday rotator and wave plate; a beam splitter coupled to receive the first beam of the first polarization from the second prism, couple light into the reference arm and the sample arm, receive a reflected beam from the sample arm and the reference arm, and provide a combined reflected beam, wherein the combined reflected beam is separated by polarization in the second prism into a first reflected beam of the first polarization and a second reflected beam of the second polarization, wherein the Faraday rotator and wave plate transmits the first reflected beam of the first polarization, and wherein the polarization dependent beam splitter couples the first reflected beam into the one or more optical detectors. In some embodiments, a power monitor can be coupled to the beam splitter. In some embodiments, the second prism couples the second reflected beam of the second polarization into the one or more detectors.

In some embodiments, the polarization dependent optics can include a linear polarizer coupled between the polarization dependent beam splitter and the light source, the linear polarizer providing a beam with a first polarization and a second polarization; a quarter waveplate coupled to receive light of the second polarization from the polarization dependent beam splitter, a mirror coupled to receive light from the quarter waveplate and reflect light back through the quarter waveplate to provide light of the first polarization to the polarization dependent beam splitter, a second quarter waveplate coupled to receive light of the first polarization from the polarization dependent beam splitter and provide circularly polarized light to the reference arm, wherein reflected light from the reference arm is light of the second polarization at the polarization dependent beam splitter; a linear polarizer oriented to pass an equal portion of light from the first polarization and the second polarization coupled to receive a combined beam from the polarization dependent beam splitter, the combined beam including light reflected from the mirror and light reflected from the reference arm; and a beam splitter coupled to receive light from the linear polarizer and provide light to the sample arm, wherein reflected light from the sample arm is coupled into the one or more detectors by the beam splitter.

In some embodiments, where the isolator is a circulator, the polarization dependent optics can include a polarization dependent beam splitter coupled to receive light from a second port of the circulator, the polarization dependent beam splitter providing a first beam; a beam splitter coupled to receive the first beam, to provide light to the sample arm and the reference arm, and receive a reflected beam from the sample arm and the reference arm, wherein a first part of the reflected beam is coupled into the one or more optical detectors by the beam splitter and a second part of the reflected beam is coupled into the polarization dependent beam splitter by the beam splitter, wherein the second part with a first polarization is coupled into the second port of the circulator, the third port of the circulator being coupled to the one or more optical detectors, and wherein the second part with a second polarization is coupled into the one or more optical detectors by the polarization dependent beam splitter.

These and other embodiments are further discussed below with respect to the following figures.

BRIEF DESCRIPTION OF THE DRAWINGS

FIGS. 5A through 5I illustrate an optical implementation of the embodiment of interferometer shown in FIG. 4.

In the figures, whenever convenient, elements having the same designation have the same or similar functions.

DETAILED DESCRIPTION

In accordance with some embodiments of the present invention, a high efficiency interferometer that can be employed on non-invasive optical imaging and measurement devices, such as optical coherence tomography and optical coherence reflectometry, is presented. Furthermore, some embodiments of optical coherence tomography devices according to the present invention can be used to image and measure biomedical tissue.

Figure 14:
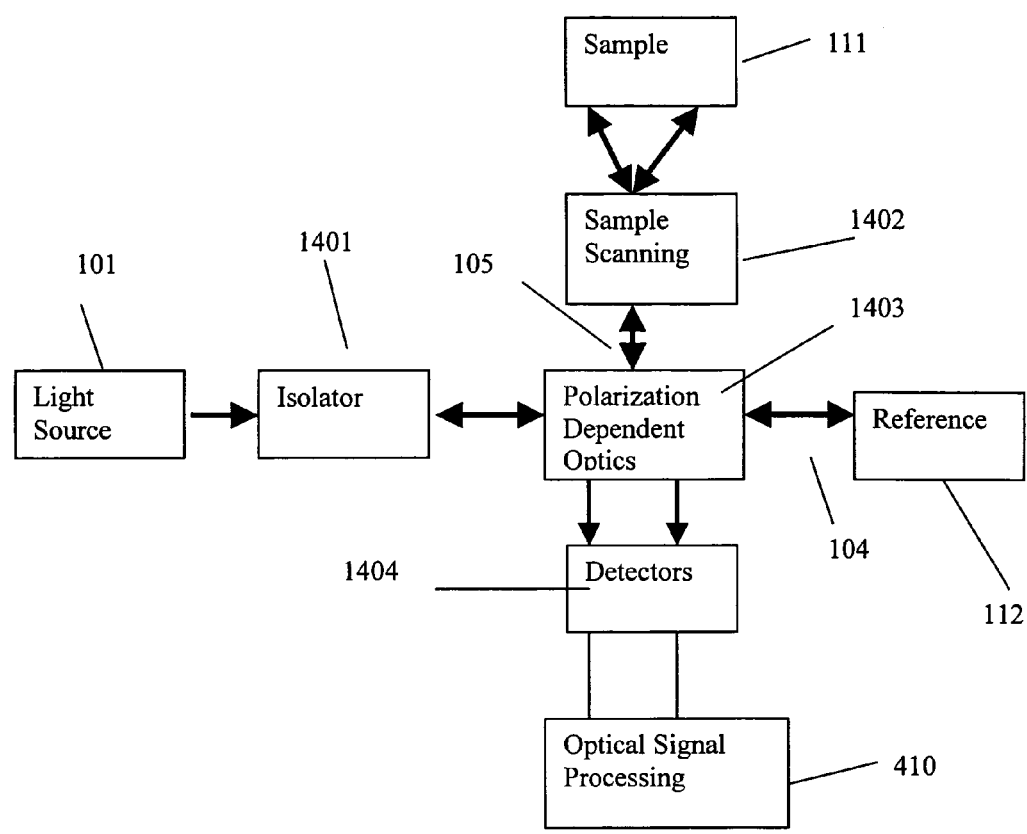
FIG. 14 illustrates aspects of embodiments of an interferometer according to the present invention.

FIG. 14 illustrates some aspects of embodiments of an interferometer according to the present invention. As discussed above, generally a Michelson interferometer includes a source arm, a reference arm, a sample arm, and a detector arm coupled by a beam splitter. Light is transmitted from the light source to the reference and the sample through the reference and the sample arms, respectively. Reflected light from the reference and the sample are combined in the detector arm and an intensity measurement of that light can be made. The data measured is related to the interference pattern created by recombining light from the reference and the sample arms and directing that light to the detector arm.

As shown in FIG. 14, an interferometer according to some embodiments of the present invention include light source 101 coupled to an optical isolator 1401. Optical isolator 1401 receives and transmits light from light source 101, but prevents light from being reflected back into light source 101. Light from isolator 1401 is then coupled to polarization dependent optics 1403. Polarization dependent optics 1403 couples light to reference arm 104 and sample arm 105 and receives reflected light from reference arm 104 and sample arm 105. Furthermore, polarization dependent optics 1403 processes optical signals such that polarization dependent effects with regard to sample 111 can be minimized in the output signal from optical signal processing unit 410. As has been discussed above, reference arm 104 is coupled to reference 112. Sample arm 105 is optically coupled to sample 111. Further, polarization dependent optics 1403 is coupled to supply reflected optical signals from reference arm 104 and sample arm 105 to detectors 1404. The output signal from detectors 1404 is then input to optical signal processing unit 410, which can provide a polarization independent signal based on the intensity of reflected light measured at detectors 1404.

In some embodiments of the invention, a sample scanning optics 1402 can be inserted into sample arm 105 so that sample 111 can be scanned. Such a scanning capability may be important, for example, in tomography applications.

Some embodiments of the current invention provide a high efficiency interferometer for optical coherence reflectometer and optical coherence tomography applications. In some embodiments of the present invention, isolator 1401 can be an optical circulator and polarization dependent optics 1403 can include a polarization beamsplitter. High efficiency performance can be achieved when a circulator and a polarization beamsplitter are coupled into the source arm of the interferometer. In some embodiments, a polarization controller 308 can be placed in reference arm 104 to produce equal reference signals in each arm of the polarization diversity interferometer. The interferometer signal generated by optical signal processing unit 410 can therefore be made independent of the polarization state of the reflected signal from sample 111, also referred to as the device under test or sample under test. An optical circulator in isolator 1401 can also provide high isolation of the reflected signal back into light source 101 to achieve high system signal to noise ratio performance. In some embodiments, an optical circulator is placed in the sample arm 105 and another optical circulator is placed in the reference arm 104. A polarization beamsplitter and polarization diversity receiver in these embodiments can be placed in the detector arm.

Some embodiments of an interferometer according to the present invention solve the problem presented by reflected light feedback into light source 101 by using optical circulators that isolate light source 101. Some embodiments of an interferometer according to the present invention solve the problem of signal dependence on the polarization state from the sample arm by using polarization diversity receivers in polarization dependent optics 1403. Some embodiments of an interferometer according to the current invention provide high power efficiency, insensitivity to the polarization state of sample arm 105, and a high signal to noise ratio for coherent domain interferometry applications. As discussed above, polarization dependence can be a result of the birefrigent characteristic of the sample material or can be due to environmental changes in the interferometer. Embodiments of high quality interferometers according to the invention can be used for a variety of purposes, such as, for example, optical coherence tomography and optical coherence reflectometry.

In some embodiments, light source 101 of the interferometer can be a broadband spectral light source and the depth resolution of the interferometer can be determined by the coherence length of the light source. In some embodiments, light source 101 can be a low coherence light source. In some embodiments, light source 101 can include a wavelength-swept source.

In some embodiments, reference 112 can include an optical delay line which can be scanned at a predetermined velocity to generate an optical path delay in the reference signal reflected from reference arm 104. In some embodiments, a 2-dimensional transverse scanning mechanism 1402 can be placed in sample arm 105 of the interferometer to scan the objects to be imaged in optical coherence tomography applications. In some embodiments, compensation can be provided for dispersion differences between sample arm 105 and reference arm 104. Several different methods are available for compensating for dispersion differences, including, for example, including a pair of prisms, a grating based optical system, and other well-known dispersion compensators that are widely employed in optical fiber telecommunication and short pulse laser applications in polarization dependent optics 1403. The dispersion compensator can be placed either in the sample or in the reference arm depending on the sign of the dispersion difference between these two arms.

In some embodiments of the current invention, light from light source 101 can be first coupled into an optical circulator and then a polarization beamsplitter before being coupled to the beamsplitter that splits the light source into sample arm 105 and reference arm 104. The ratio of the beamsplitter can be chosen to maximize the light reflected from sample arm 105 into the optical circulator and at the same time still keep enough light intensity from reference arm 104 reflected back into the optical circulator.

In some embodiments of interferometer according to the present invention, light source 101 can be a fast wavelength swept coherent light source. In some embodiments, reference 112 can be a fixed reflector. In some embodiments, the principles of Optical Frequency-Domain Reflectometry can be utilized.

In some embodiments of interferometer according to the present invention, the image distance is insensitive to the motion of sample 111. Further, in some embodiments of interferometer according to the present invention, the signal strength measured at detectors 1404 can be insensitive to polarization changes.

Figure 1:
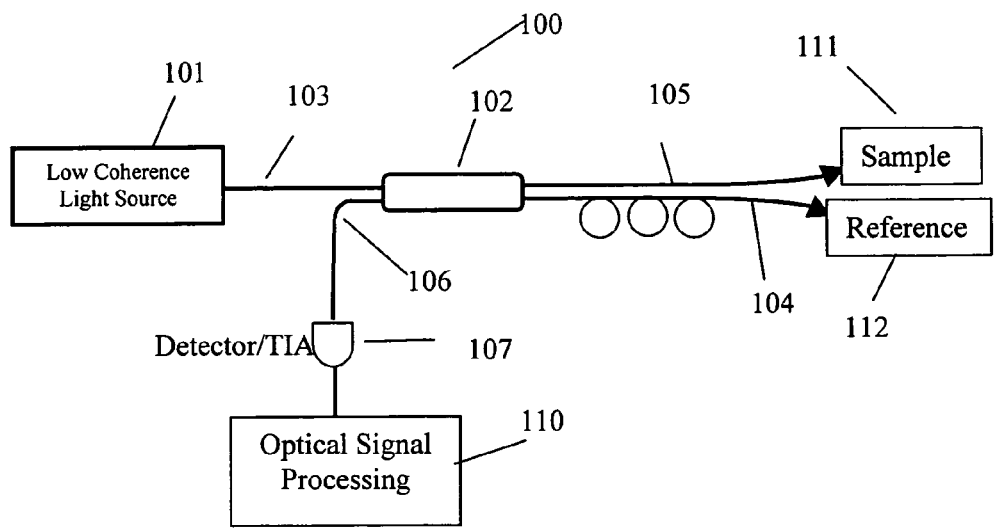
FIG. 1 illustrates a conventional low coherence interferometer with a Michaelson interferometer configuration.
Figure 2:
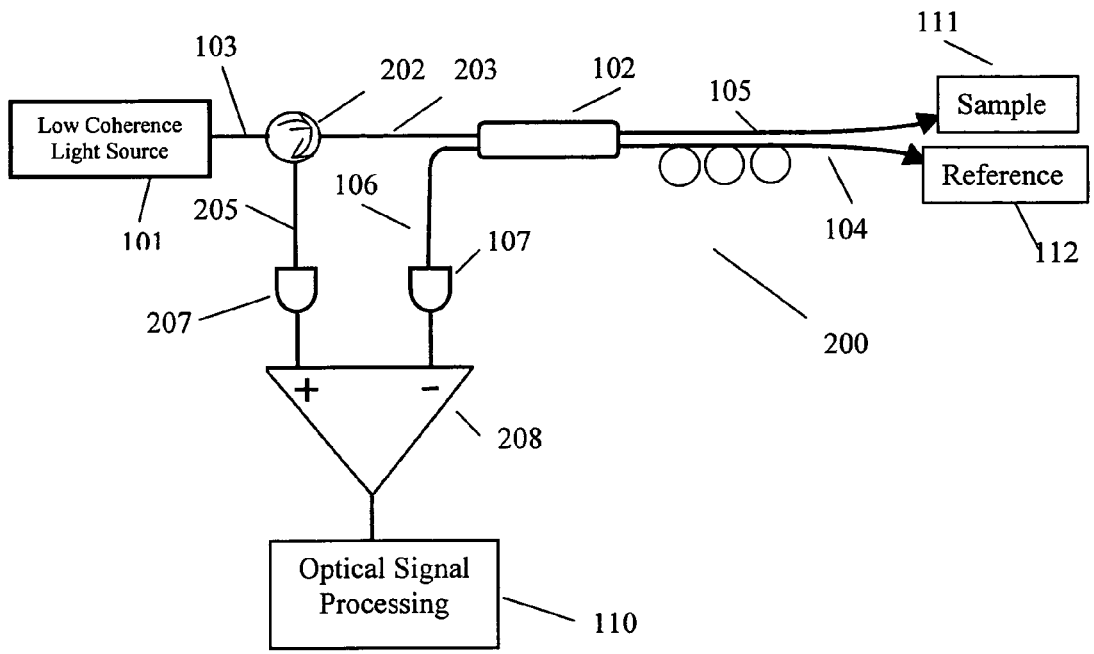
FIG. 2 illustrates a conventional low coherence interferometer with an optical circulator in the source arm and a balanced detector in the detector arm.
Figure 3:
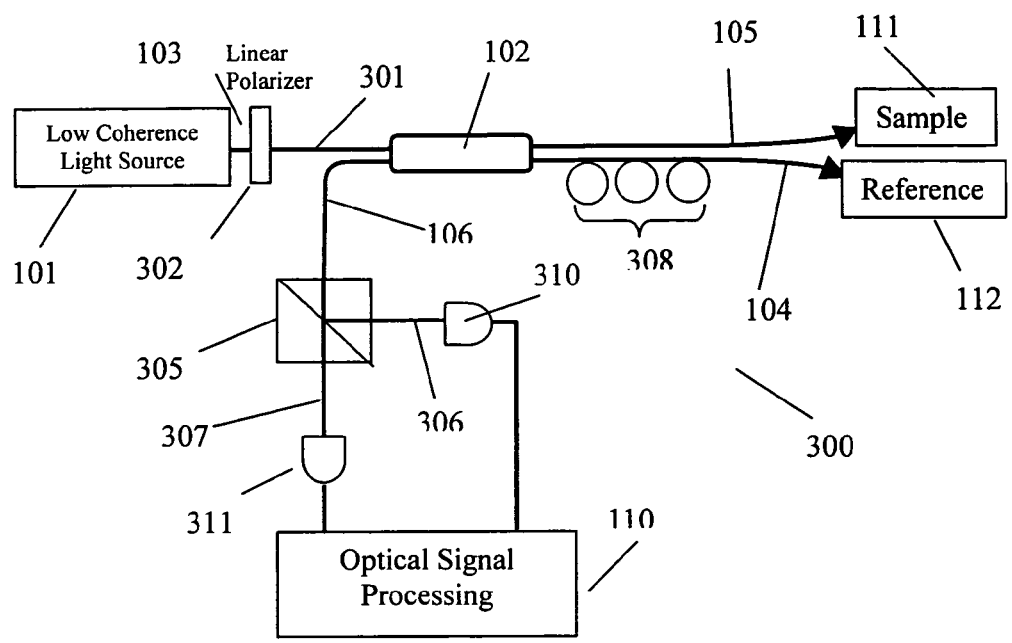
FIG. 3 illustrates another low coherence interferometer with a linear polarizer in the source arm to polarize the light source of the Michaelson interferometer and a polarization diversity receiver in the detector arm.
Figure 4:
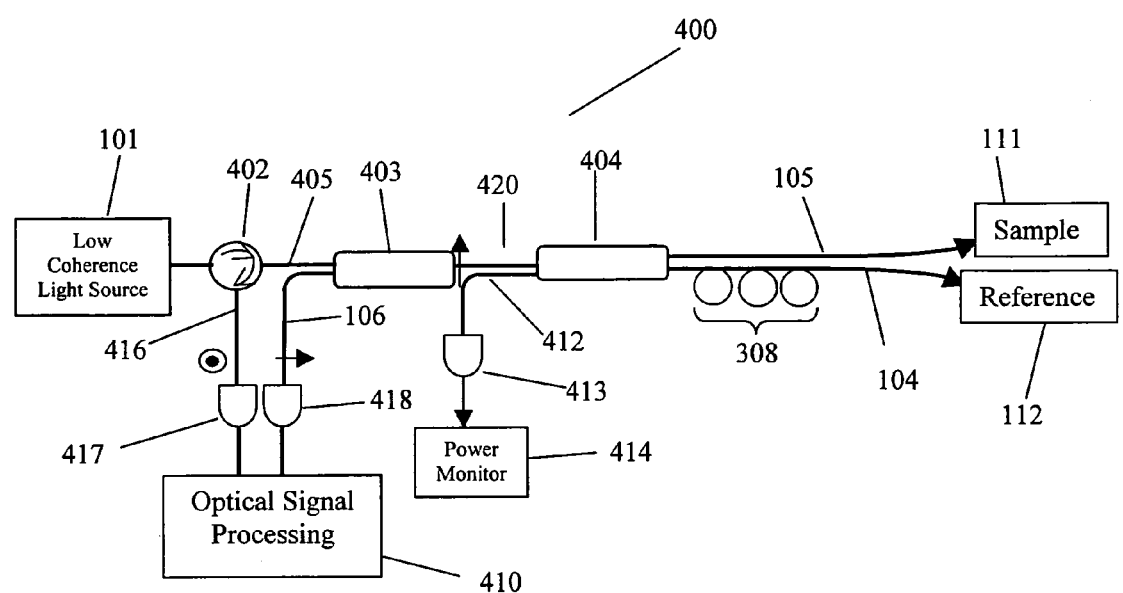
FIG. 4 illustrates an embodiment of an interferometer according to some embodiments of the current invention with an optical circulator and polarization beam splitter in the source arm and polarization diversity detection in the interferometer.

FIG. 4 illustrates an embodiment of interferometer according to the present invention. As shown in FIG. 4, some embodiments of the present invention use polarization effects to route optical beams into particular optical paths. The embodiment illustrated in FIG. 4 includes a separation of paths for two orthogonal polarization states to generate interference signals where the two orthogonal polarization states can be processed separately to achieve high efficiency, polarization-independent interferometry performance.

As shown in FIG. 4, interferometer 400 includes light source 101. Light from light source 101 is first coupled into port 1 of an optical circulator 402. In the embodiment shown in FIG. 4, optical isolator 1401 includes circulator 402.

Optical circulator 402 is a polarization independent optical device, so all light in all polarization states that enter port 1 will exit from port 2 of optical circulator 402 into source arm 405 of interferometer 400. Light from source arm 405 is then coupled into polarization dependent beam splitter 403. In polarization dependent beam splitter 403, light from source arm 405 is polarized into two linear polarized light beams, denoted as P and S Polarization.

As is conventionally denoted, in a propagating optical wavefront, S polarization light has its electric field vector normal to the plane of incidence and P polarization light has its electric field vector parallel to the plane of incidence. The plane of incidence is parallel to the paper in all drawings shown in this disclosure. Only P-polarized light will be coupled into beam path 420 and therefore into an optical beamsplitter 404 that is coupled to beam splitter 403 through beam path 420. The S-polarized Light will be discarded by being coupled into another beam path from beam splitter 403 or may be utilized to monitor power.

In some embodiments of the present invention, the optical components can be formed in bulk optics. However, some embodiments may utilize fiber optic components (i.e., components formed into or as part of the optical fibers). Fiber optic components have the advantage of minimizing misalignments.

Most low coherent light sources, such as low coherence light source 101 in some embodiments, are only partially polarized. To achieve maximum efficiency, light source 101 can be rotated such that the most polarized light is aligned to be parallel to the plane of incidence (P polarization) when coupled into polarization beam splitter 403.

The splitting ratio of beam splitter 404 can be optimized such that most of the light will propagate into sample arm 105 and only enough light will propagate into reference arm 104 to perform the appropriate measurements. The splitting ratio can be determined by the reflectance of the optical delay scanner and total transmission of the light reflected from reference path 104 of interferometer 400. The light reflected by reference 112 in reference arm 104 should be more intense than the light reflected from sample 111 in sample path 105 in order to achieve shot noise limited detection performance. Since the reflection from reference 112 corresponding to sample 111, where sample 111 can be biological tissue, is normally very small compare to the reflectance of reference 112, a typical 90/10 splitting ratio with 90 percent of the light received on source arm 420 being directed to sample arm 105 and 10 percent being directed to reference arm 104 can be utilized for shot noise performance.

As is well understood by those skilled in the art, reference 112 can include, for example, reflective components and optical delay components. Further, in some embodiments reference 112 can also include a scanning capability which can be coupled with optical signal processing unit 410.

A small amount of light reflected from sample 111 and reference 112 can be coupled into optical path 412 by splitter 404. This small amount light can be coupled into detector 413 and the electrical signal from detector 413 coupled into power monitor circuit 414. This amount of light can therefore be utilized to monitor the optical power reflected from sample 111 and reference 112. A similar circuit can be coupled to beam polarization beam splitter 403 in order to monitor power based on the S polarized light output by polarization beam splitter 403.

The light reflected from sample 111 and reference 112 typically contains both S-polarized and P-polarized light due to optical properties of sample 111 and reference 112. Polarization dependent beam splitter 403 again will split the S-Polarized and P-polarized light components into two separate paths 106 and 405. Polarization controller 308 in reference arm 104 can be adjusted to generate equal amounts of P-polarization light in P-polarization path 106 and S-polarized light in S-polarization path 405 from reference 112. Polarization controller 308, in some embodiments, can be made of three optical fiber loops with each loop corresponding to a quarter wave plate or other polarization-dependent optical device.

Light coupled back into source arm 405 by polarization dependent beam splitter 403, the S-polarization light component, is routed into path 416 by circulator 402, thereby isolating low coherence light source 101. Such an arrangement reduces noise resulting from coupling of light from interferometer 400 back into light source 101.

Like light from reference path 104, the S-polarized light from sample arm 105 will propagate into optical path 416 and the P-polarized light from sample arm 105 will propagate into optical path 106. The interference signals in each of polarization path 416 and 106 are received by photo detectors 417 and 418, respectively. The electrical signals from photodetectors 417 and 418 are then individually processed in optical signal processing unit 410. In some embodiments, optical signal processing unit 410 can output a combined signal indicating the sum of the intensity of light measured by detectors 417 and 418. The signal output from optical signal processor 410 can be the sum of P-polarized and S-polarized interference components so that, through processing, the signal strength indicated by the output signal from optical signal processing 410 is independent of the polarization states of light reflected from sample 111 in sample arm 105. This feature of this embodiment is advantageous, especially when the sample is highly birefringent, like biological tissue composed of collagen fiber, for example.

Figure 5A:
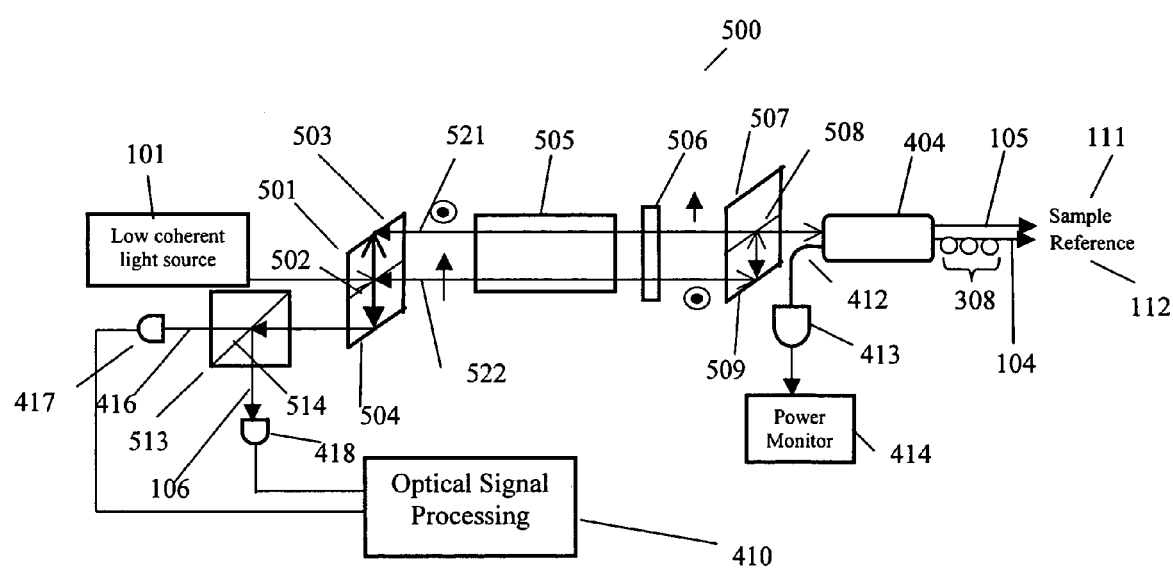

FIG. 5A illustrates an embodiment of an interferometer 500 according to the present invention. As shown in FIG. 5A, light from light source 101 is split by a prism 501 into S-polarized and P-polarized optical beams because of a polarization beamsplitter coating surface 502 on prism 501. Although shown as a prism, prism 501 can be any polarization beam splitting device. The S-polarized beam is reflected from surface 502 and reflected by a mirror or preferred total internal reflection (TIR) surface 503. The S-polarized beam 521 is rotated 45 degree counter-clockwise (CCW) by a Faraday rotator 505 when observing beam 521 against the direction of propagation. It is well known that the Faraday effect, which rotates an optical beam, depends on the direction of a magnetic field on the Faraday rotator and the angle of rotation depends on the magnitude of the magnetic field on the Faraday rotator. The Faraday effect process is non-reciprocal, which means that the rotation does not depend on the direction of propagation of the beam.

A $\lambda/2$ wave plate 506 is oriented 22.5 degrees to the vertical axis and positioned behind Faraday rotator 505. The beam output from Faraday rotator 505, then, will rotate another 45 degrees and become a P-polarized beam after passing through $\lambda/2$ wave plate 506. FIGS. 5B through 5E illustrate the polarization rotations that light from light source 101 undergoes passing through prism 501, Faraday rotator 505, and $\lambda/2$ wave plate 506. FIG. 5B illustrates the S-polarized beam 521 output from prism 501. FIG. 5C shows the 45° counter-clockwise rotation of the beam output from Faraday rotator 505. FIG. 5D illustrates the rotation through $\lambda/2$ wave plate 506. FIG. 5E illustrates the resulting P-polarized beam input to prism 507. The P-polarized beam then will transmit through the polarizing beamsplitter coating surface 508 of prism 507.

On the other hand, the P-polarized beam 522 will also be rotated 45 degree by the Faraday rotator 505 and then rotated onto an S-polarized beam by $\lambda/2$ wave plate 506. The S-polarized light is reflected by surface 509 (mirror or TIR) and surface 508 of prism 507 into beamsplitter (or coupler) 404. In this configuration, both S-polarized and P-polarized light from light source 101 is coupled into beam splitter 404.

FIGS. 5F through 5I illustrate the polarization rotations undergone by light reflected from sample 111 and reference 112. The S-polarized component of light reflected either from reference 112 or sample 111 propagates through surface 508 of prism 507, surface 509 of prism 507, $\lambda/2$ wave plate 506, and Faraday rotator 505 before being coupled into prism 501. As described previously, since the Faraday effect is non-reciprocal, the S-polarization is still orientated on the S-polarization plane after passing through the above optical path. The S-polarized light will be reflected from surface 502, and then surface 504 of prism 501, and reflected from polarizing splitter coating surface 514 of polarization beam splitter 513 before being received by photo detector 418. FIG. 5F shows a S-polarized beam. FIG. 5G illustrates the rotation of the S-polarized beam after passing through $\lambda/2$ wave plate 506. FIG. 5H illustrates the rotation that the beam undergoes after passing through Faraday rotator 505. Finally, FIG. 5I illustrates the S-polarized beam incident on polarization dependent beam splitter 513.

The P-polarized component of light reflected down either reference arm 104 or sample arm 105 will also propagate through $\lambda/2$ wave plate 506 and Faraday rotator 505, without changing polarization. The P-polarized component reflects from surface 503, and passes through surface 502, surface 504, and surface 514, before it is received by photo detector 417. Polarization controller 308 can be adjusted to generate equal S-polarized and P-polarized reference light in optical path 106 and 416 for polarization diversity detection. The two orthogonally polarized light beams can then be individually demodulated and processed before being processed into an overall intensity signal in optical signal processing unit 410.

In the embodiment shown in FIG. 5A, an isolator such as isolator 1401 in FIG. 14 includes prism 501 and polarization dependent optics such as polarization dependent optics 1403 in FIG. 14 includes prism 501, Faraday rotator 505, $\lambda/2$ wave plate 506, prism 507, beam splitter 404, and polarization dependent beam splitter 513.

Figure 6:
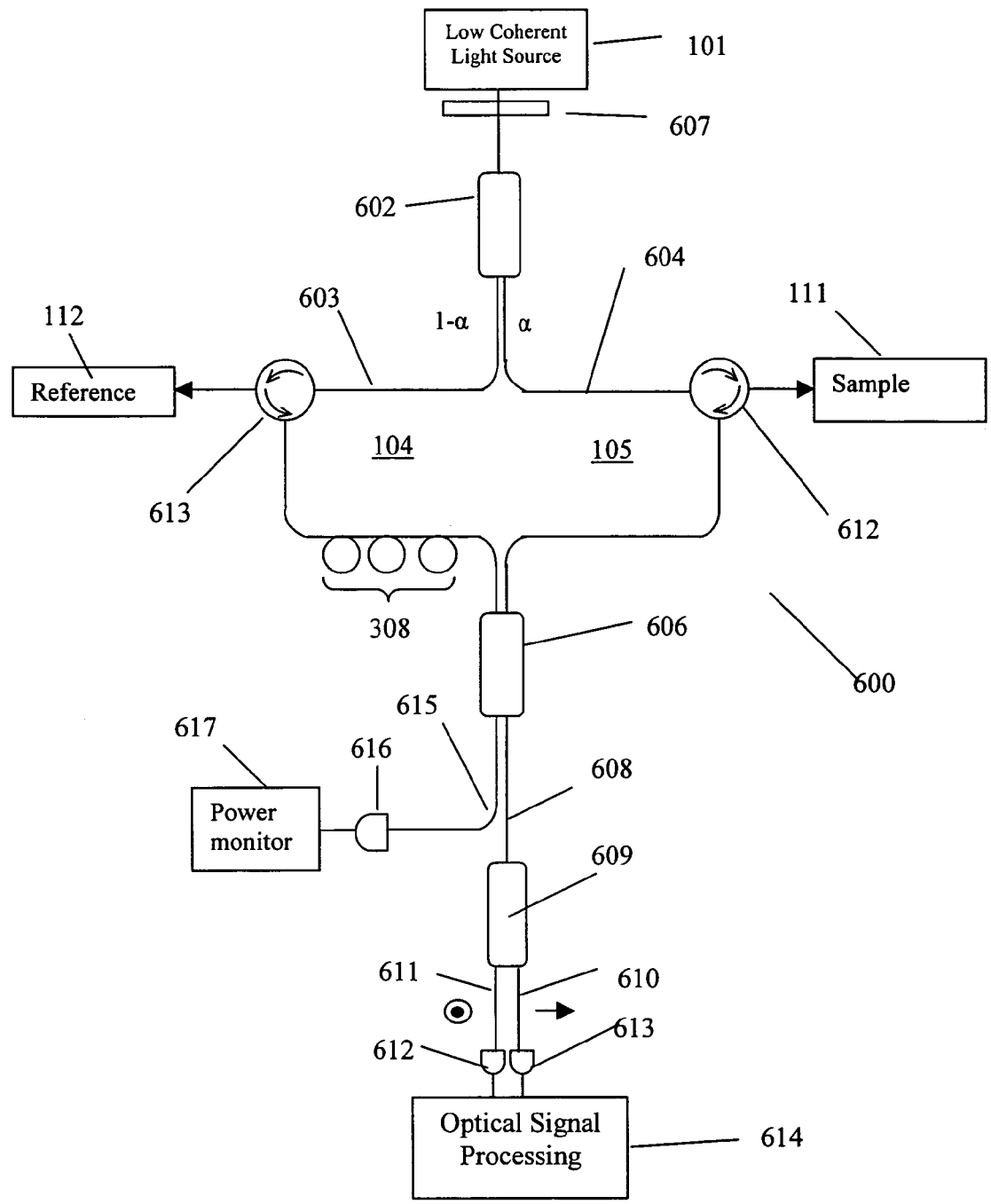
FIG. 6 illustrates an embodiment of an interferometer according to the present invention with optical circulator in both sample and reference arm and polarization diversity detection.

FIG. 6 illustrates another embodiment of an interferometer according to the present invention. Interferometer 600 as shown in FIG. 6 can increase optical efficiency and reduce light reflection feedback into light source 101 with two optical circulators 612 and 613. Optical circulator 613 is positioned in reference arm 104. Optical circulator 612 is positioned in sample arm 105. Interferometer 600 shown in FIG. 6 is similar to a conventional Mach-Zhender interferometer. Light from light source 101 is input to linear polarizer 607. Beam splitter 602 splits the linear polarized light received from polarizer 607. As shown in FIG. 6, an amount of light α is directed into sample arm 105 and the remainder of the light, 1−α, is directed into reference arm 104. The splitter ratio of beam splitter 602 can, in some embodiments, be determined by the relative efficiencies of the beam paths.

In reference arm 104, light is directed into a first port of circulator 613. Light exiting from a second port of circulator 613 is then directed into reference 112 and the reflected light from reference 112 is again directed into the second port of circulator 613. Light exiting the third port of circulator 613 is directed into polarization controller 308. Light exiting polarization controller 308 is input to beam splitter 606.

Similarly, light in sample arm 105 is first directed into a first port of circulator 612. Light exciting a second port of circulator 612 is coupled to sample 111. Reflected light from sample 111 then is coupled back into the second port of circulator 612. Light exiting the third port of circulator 612 is directed into beam splitter 606.

Light from reference arm 104 and light from sample arm 105 is then combined in beam splitter 606 and directed into beam path 608. Beam path 608 couples light into polarization dependent beam splitter 609. Polarization dependent beam splitter 609 splits the light beam into an S-polarized beam that is coupled into beam path 611 and a P-polarized beam that is coupled into beam path 610. In some embodiments of the invention, polarization controller 308 can be adjusted to generate equal intensities of S-polarized and P-polarized reference light in optical paths 611 and 610, respectively, for polarization diversity detection.

As shown in FIG. 6, the intensity of the light beam in beam path 611 is detected in optical detector 612 and the intensity of the light beam in beam path 610 is detected in optical detector 613. The electrical signals generated in detectors 612 and 613 are input to optical signal processing unit 614. In some embodiments, the P-polarization interference signal measured at detector 613 and S-polarization interference signal measured at detector 612 are individually demodulated and processed before being summed in an overall interference signal output by optical signal processing unit 614.

As further shown in FIG. 6, a portion of the mixed light from beam splitter 606 can be coupled into beam path 615 and detected by detector 616. The electrical output signal from detector 616 can then be input to power monitor 617.

In the embodiment shown in FIG. 6, an isolator such as isolator 1401 in FIG. 14 includes circulator 613 and circulator 612. Further, polarization dependent optics such as polarization dependent optics 1403 in FIG. 14 includes linear polarizer 607, beam splitter 602, beam splitter 606, and polarization beam splitter 609.

Figure 7:
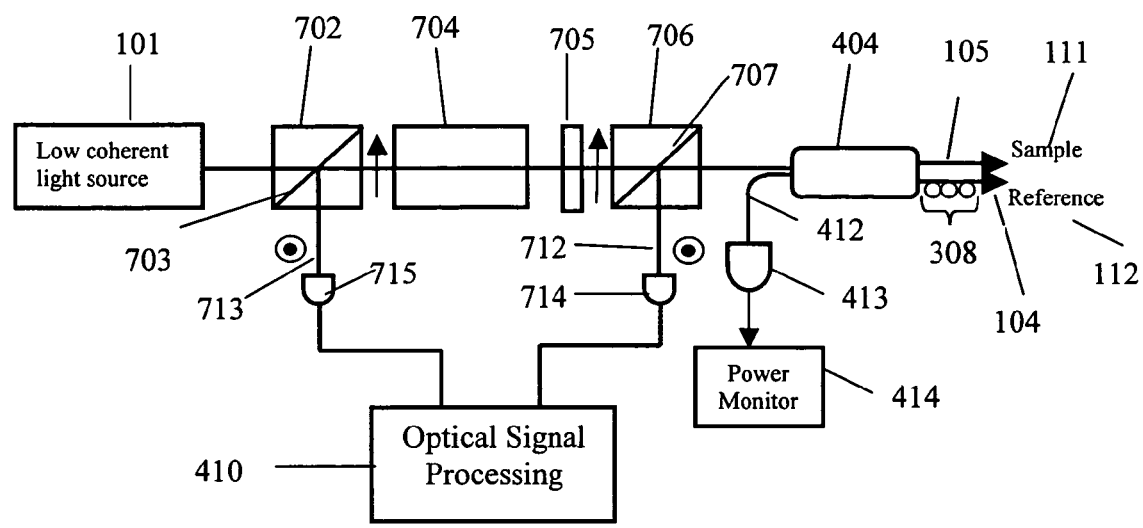
FIG. 7 illustrates an embodiment of an interferometer according to the present invention with two polarization beam splitters, a Faraday rotator, and a wave plate.

FIG. 7 illustrates another interferometer 700 according to some embodiments of the present invention. As shown in FIG. 7, light from light source 101 is first polarized by a polarizing beamsplitter surface 703 of polarization beam splitter 702. The S-polarized light is reflected from surface 703 and can be discarded or utilized in power monitoring. To minimize the loss of light, light source 701, which may be partially polarized, can be rotated to maximize the light intensity of P-polarized light entering polarizing beam splitter 702. A Faraday rotator 704 and a $\lambda/2$ wave plate 705 can be arranged such that the P-polarized light remains P-polarized when it exits $\lambda/2$ wave plate 705. The P-polarized light, then, is transmitted through polarizing beamsplitter coating surface 707 of polarization beam splitter 706 and is coupled into beam splitter 404. Beam splitter 404 couples light into sample arm 105 and reference arm 104, as has been discussed above.

The reflected S-polarized light from beam splitter 404 (which is a combination of the S-polarized light reflected from sample 111 and reference 112) is reflected from surface 707 of polarization beam splitter 706 into optical path 712. The P-polarized light from beam splitter 404 (which is a combination of the P-polarized light reflected from sample 111 and reference 112) is transmit through polarization beam splitter 706 and rotated into S-polarized light by the combination of λ/2 waveplate 705 and Faraday rotator 704. The S-polarized light will be reflected into optical path 713 from surface 703 of polarization beam splitter 702. The optical beam in signal path 712 is detected in detector 714 and the optical beam in signal path 713 is detected in detector 715. The electrical signals from detectors 714 and 715 are then coupled into optical signal processing unit 410. The two interference signal paths, signal path 713 which contains P-polarization information of sample 111 and optical path 712 which contains S-polarization information of sample 111, are individually received, demodulated, and processed before being summed into an overall intensity signal by optical signal processing unit 410.

As was discussed previously, a small amount of light reflected from sample 111 and reference 112 can be diverted to detector 413 through optical path 412. Therefore, power monitor 414 can monitor the intensity of the overall reflected light from reference arm 104 and sample arm 105.

In some embodiments, the power of light source 101 itself can be monitored by adding a power monitoring device to detect the S-polarized light reflected out of prism 702, for example. Such a power monitor would be unaffected by reflected light from sample 111.

In the embodiment shown in FIG. 7, an isolator such as isolator 1401 in FIG. 14 includes polarization beam splitter 702, Faraday rotator 704, and λ/2 waveplate 705. Furthermore, polarization dependent optics such as polarization dependent optics 1403 in FIG. 14 includes polarization beam splitter 702, Faraday rotator 704, λ/2 wave plate 705, polarization beam splitter 706, and beam splitter 404.

Figure 8:
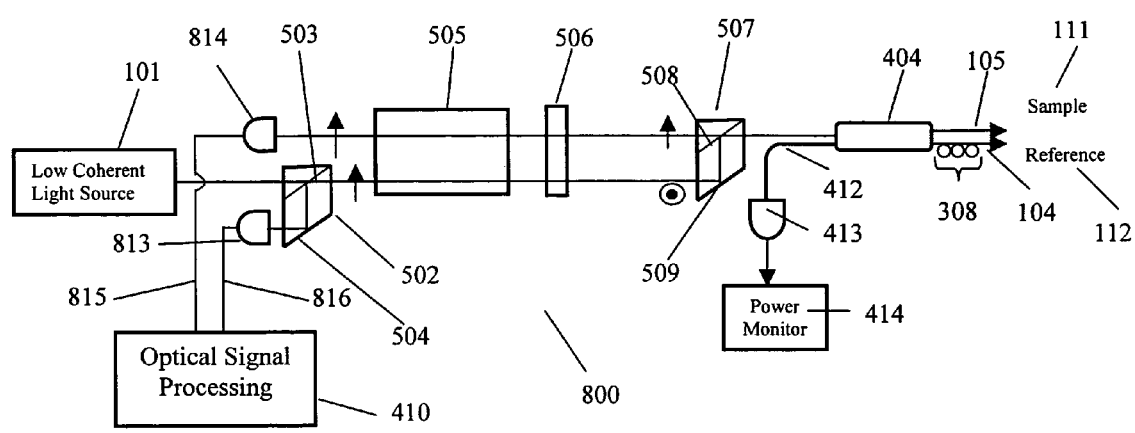
FIG. 8 illustrates an embodiment of an interferometer according to the present invention with prisms, a Faraday rotator, and a wave plate.

FIG. 8 illustrates an interferometer 800, which illustrates another embodiment of interferometer according to the present invention. In comparison with the embodiment of interferometer 500 shown in FIG. 5, polarization beam splitter 513 is eliminated in interferometer 800. The light from light source 101 enters prism 502 and is polarization split by the polarization beamsplitter coating surface 503. The S-polarization light is reflected from surface 503 and is therefore discarded or utilized for power monitoring. The P-polarized light propagates through surface 503 of polarization beam splitter 502 and is rotated into S-polarization light by the combination of Faraday rotator 505 and λ/2 wave plate 506. The S-polarized light is reflected from surface 509 (mirror or TIR) and polarization beamsplitter coating surface 508 of prism 507 into beam splitter 404. As discussed before, beam splitter 404 splits the light into sample arm 105 and reference arm 104. As previously discussed, the splitting ratio of beam splitter 404 can be set to optimize performance.

The combined S-polarized light reflected from sample arm 105 and reference arm 104 propagates through the reverse path as that described above in prism 507. The combination of λ/2 wave plate 506 and Faraday rotator 505 does not change the polarization orientation of the S-polarized light entering from prism 507, as has been discussed previously. Therefore, the S-polarized light reflected from surface 503 and 504 of prism 502 can be coupled into photo detector 813. The combined P-polarized light reflected from sample arm 105 and reference arm 104 will propagate through the surface 508, λ/2 wave plate 506, and Faraday rotator 505 along different optical paths than the S-polarized light, as shown in the FIG. 8. The P-polarized light, then, can be coupled into photo detector 814. The electrical signal 816 from detector 813, then, corresponds with the intensity of the S-polarized signal from sample 111 and reference 104 and the electric signal 815 from detector 814 corresponds to the P-polarized signal from sample 111 and reference 104. Interference signals 815 and 816 can be individually demodulated and processed before being summed to represent the total interference intensity in optical signal processing unit 410. As before, polarization controller 308 can be adjusted to provide equal light power as indicated by signals 815 and 816 for polarization diversity detection.

In the embodiment shown in FIG. 8, an isolator such as isolator 1401 can include prism 502, Faraday rotator 505, and λ/2 wave plate 506. Further, polarization dependent optics such as polarization dependent optics 1403 includes prism 502, Faraday rotator 505, λ/2 wave plate 506, prism 507, and beam splitter 404.

Figure 9:
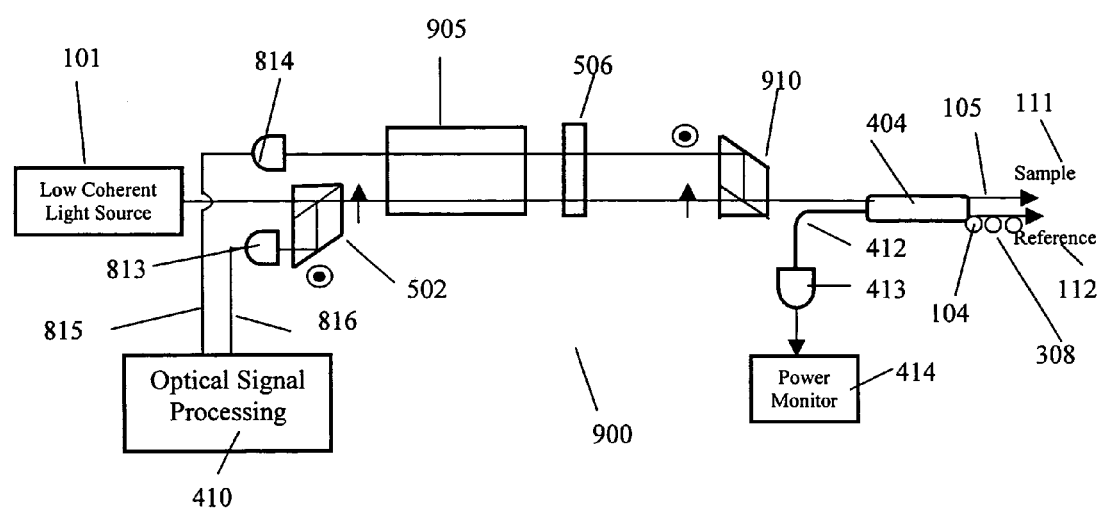
FIG. 9 illustrates an embodiment of an interferometer according to the present invention with prisms, a Faraday rotator, and a wave plate.

FIG. 9 illustrates another interferometer 900 according to some embodiments of the present invention. Interferometer 900 is similar to interferometer 800, with a similar arrangement of Faraday rotator 905, λ/2 plate 506, and prism 502. In interferometer 900, however, prism 910 is oriented so as to let P-polarized light transmit through prism 502, Faraday rotator 905, and λ/2 wave plate 506 without changing polarization. The magnetic field of Faraday rotator 905 is reversed in direction from that of Faraday rotator 505. The S-polarized components from either sample arm 105 or reference arm 104 will reflect from prism 502 into detector 813. The P-polarized components will propagate through the incident beam path and into detector 814. All other operations are the same as previously described.

In the embodiment shown in FIG. 9, an isolator such as isolator 1401 includes prism 502, Faraday rotator 905, and λ/2 wave plate 506. Further, a polarization dependent optics such as polarization dependent optics 1403 includes prism 502, Faraday rotator 905, λ/2 wave plate 506, prism 910, and beam splitter 404.

Figure 10:
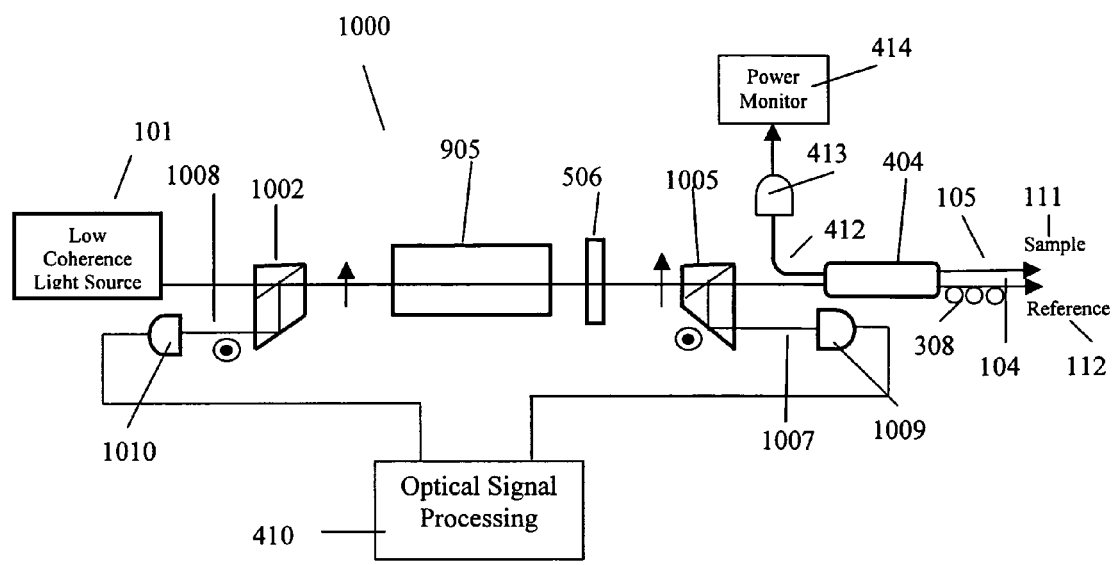
FIG. 10 illustrates an embodiment of an interferometer according to the present invention with prisms, a Faraday rotator, and a wave plate that are symmetrically arranged.

FIG. 10 shows an embodiment of interferometer 1000, which is another embodiment of interferometer according to some embodiments of the present invention. Interferometer 1000 is similar to the embodiments of interferometer shown in FIGS. 8 and 9, but with a symmetrical optical arrangement. The P-polarized component of light source 101 transmits through the prism 1002, Faraday rotator 905, λ/2 wave plate 506, and prism 1005 into beam splitter 404. In the reflection path, the S-polarized component will be reflected from prism 1005 into optical path 1007. The P-polarized component will be rotated into S-polarized light by λ/2 wave plate 506 and Faraday rotator 905 and reflected by prism 1002 into optical path 1008. Again, the light beam in beam path 1007 is detected by detector 1009 and the light beam in beam path 1008 is detected in detector 1010. Optical signal processing unit 410, then, again, receives one signal corresponding to P-polarized light reflected from sample 111 and one signal corresponding to S-polarized light reflected from sample 111.

In the embodiment shown in FIG. 10, an isolator such as isolator 1401 can include prism 1002, Faraday rotator 905, and λ/2 wave plate 506. Further, a polarization dependent optics such as polarization dependent optics 1403 can include prism 1002, Faraday rotator 905, wave plate 506, prism 1005, and beam splitter 404.

Figure 11:
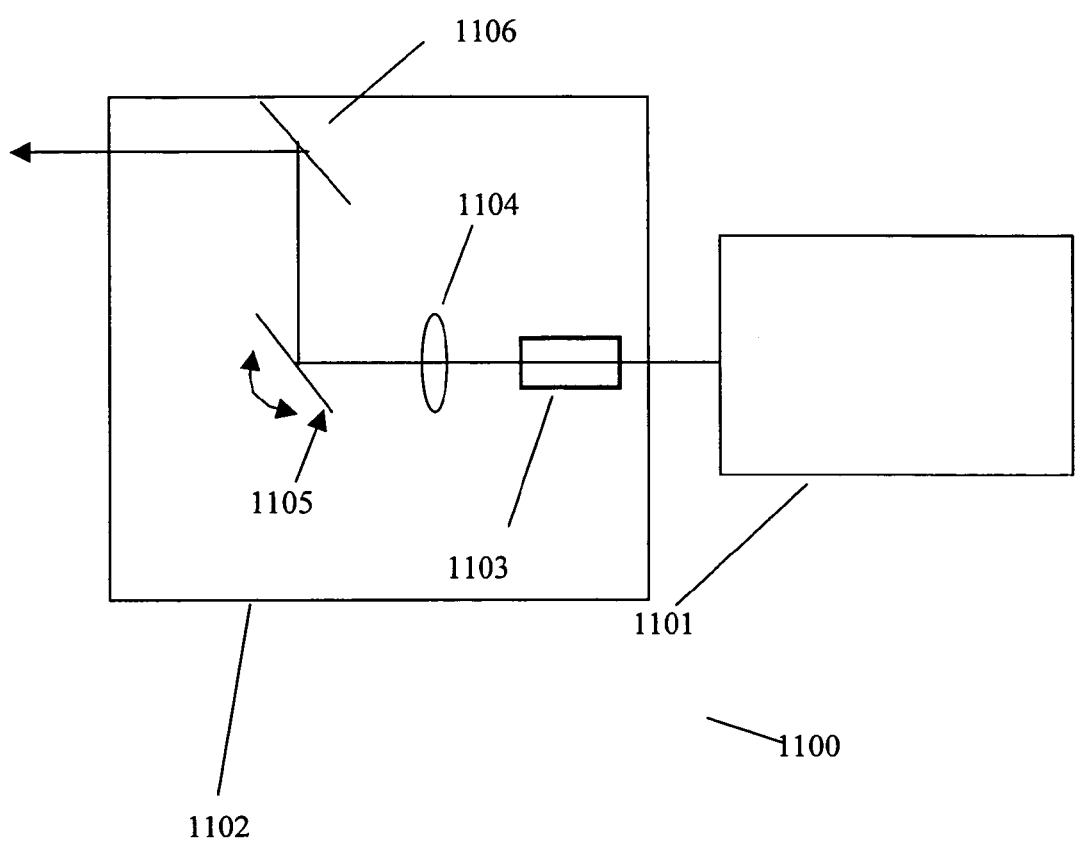
FIG. 11 illustrates an embodiment of a fast wavelength sweep light source that can be utilized in an interferometers according to some embodiments of the present invention.

FIG. 11 illustrates a light source 1100 that can replace low coherent light source 101 such as that shown in the embodiments of the invention illustrated in FIGS. 4, 5A, 6, 7, 8, 9, and 10. Light source 1100 employs a coherent light source 1101 such as a laser. The wavelength of the coherent light source can be rapidly swept through a broad wavelength range by scanning a scanner 1102, which includes an optical grating 1005 and reflector 1106, and reflecting the light from an optical mirror 1106. As shown in FIG. 11, the beam from laser 1101 can be collimated in collimator 1103 and shaped or focused in lens system 1104 before being incident on grating 1105. One skilled in the art will realize that there are number of configurations of fast wavelength sweep light source 1100 that can be utilized in embodiments of the present invention. The light source 1100 may be coupled to any embodiment of interferometer, including those disclosed in FIGS. 4 through 14. In such embodiments, reference 112 may not include an optical delay.

Figure 12:
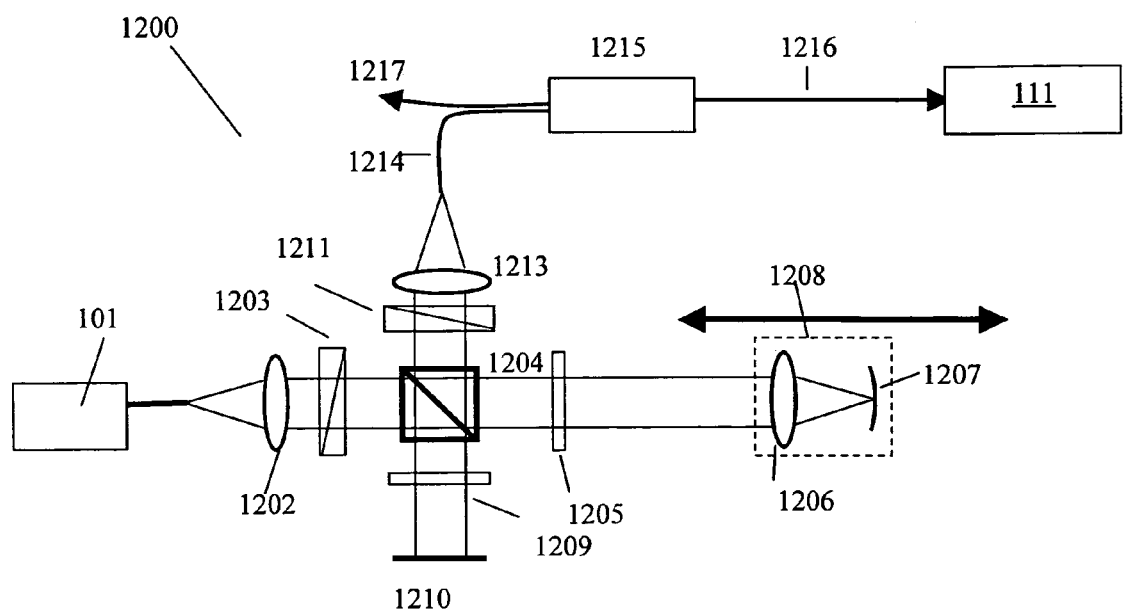
FIG. 12 illustrates an embodiment of a double beam interferometer according to the present invention that is insensitive to the polarization states and insensitive to the motion of the sample.

FIG. 12 illustrates an embodiment of interferometer 1200, which is another embodiment of interferometer according to the current invention. Interferometer 1200 can employ a low coherence light source 101 or, in some embodiments, can employ a light source such as that illustrated in FIG. 11. The light is first collimated by collimator 1202 and then polarized by a linear polarizer 1203. Polarizer 1203 can be oriented, together with a polarization beam splitter 1204, to split the light into a particular ratio between S and P. polarization. The S-polarization beam is reflected by polarization beam splitter 1204 and passes thorough a quarter waveplate 1209 with the optical axis at 45 degree to the beam propagation direction. Once passing through quarter waveplate 1209, the beam becomes circular polarized. Upon reflection by the mirror 1210, the beam changes handedness (e.g., a counter-clockwise circularly polarized beam becomes a clockwise circularly polarized beam). A second pass through quarter waveplate 1209 from the direction of mirror 1210 causes the beam to become P-polarized.

The original P-polarized beam is transmitted through polarization beam splitter 1204, is circularly polarized by quarter wave plate 1205, and is reflected by retroreflection optical assembly 1208 to arrive back at polarization beam splitter 1204 as a S-polarized beam through a similar optical configuration and return back to the polarization beam splitter 1204, in S-Polarization. As shown in FIG. 12, retroreflection optical assembly 1208 can include a lens 1206 and a concave mirror 1207 or simply a corner cube. The two beams, a P-polarized beam reflected from mirror 1210 and a S-polarized beam reflected from retroreflection optical assembly 1208, are combined by polarization beam splitter 1204 and are coupled into a linear polarizer 1211 that is oriented at 45 degrees to the optical axis. The beam will be focused into the source arm 1214 of an optical beamsplitter 1215 by lens 1213. The beam is then coupled to sample arm 1216 and onto sample 111. The beam reflected from sample 111 will be reflected into detector arm 1217, where its intensity can be detected by a detector and the resulting electrical signal input to an optical signal processor.

Beamsplitter 1215 can be made with a bulk optics such that the focusing lens 1213 is not necessary in some embodiments. By changing the location of retroreflector assembly 1208, an optical distance can be measured. Furthermore, if a transverse scan mechanism is integrated into sample arm 1216 of the beam, a cross sectional image of the sample can be acquired. Since the light beams of each polarization type are interfered separately from two surfaces of sample 111, the measurement is in-sensitive to the motion of the sample. Also, since the signal is the sum of both polarization types, the signal strength is insensitive to the polarization change in the interferometer.

In the embodiment shown in FIG. 12, an isolator such as isolator 1401 from FIG. 14 includes polarizer 1203, polarization beamsplitter 1204, and quarter waveplates 1209 and 1204. Further, polarization dependent optics such as polarization dependent optics 1403 includes polarizer 1203, polarization beam splitter 1204, quarter waveplate 1209, and linear polarizer 1211.

Figure 13:
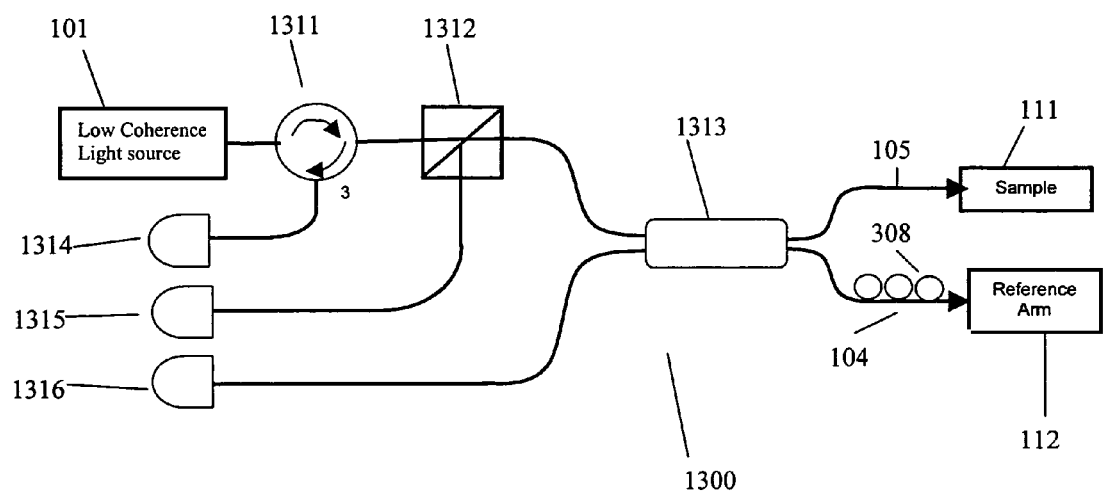
FIG. 13 illustrates an embodiment of an interferometer according to the present invention.

FIG. 13 illustrates an interferometer 1300, which is another embodiment of the present invention that uses balance detection to reduce the noise from light source 101. Further, the signal output by an optical signal processor can be independent of polarization state change in the system and sample tissue of sample 111 in this embodiment. Interferometer 1300 can utilize a low coherence light source for light source 101 or a light source such as that shown in FIG. 11. The light enters into port 1 of circulator 1311 and exits at port 2 of circulator 1311. The light beam from circulator 1311 is polarized by polarization beam splitter 1312. The S polarized light exits from polarization beamsplitter 1312 and, in some embodiments, can be utilized for power monitoring. The P polarized light from polarized beam splitter 1312 is then coupled into fiber beam splitter 1313, which couples light into sample arm 105 and reference arm 104. In some embodiments, fiber beam splitter 1313 can couple the light into sample arm 105 and reference arm 104 equally. Reflected light from sample 111 and reference 112 is received by beam splitter 1313. In some embodiments, half of the light reflected back into beam splitter 1313 will be coupled to detector 1316. The other half of the reflected light is coupled into polarization beam splitter 1312 to be split between detector 1314 and detector 1315 according to the polarization state of light when it reaches polarization beam splitter 1312.

In the embodiment shown in FIG. 13, an isolator such as isolator 1401 includes circulator 1311. Furthermore, a polarization dependent optics such as polarization dependent optics 1403 includes polarization beam splitter 1312 and beam splitter 1313.

If interferometer 1300 is arranged to the following conditions:

1) The light reflected back from sample 111 has intensity much less than the light reflected from reference 112;

2) Polarization controller 308 in reference arm 104 is adjusted so that detector 1314 and detector 1315 receive the same optical intensity from reference arm 104;

3) There is substantially no excess loss of optical radiation in circulator 1311, polarization beam splitter 1312, and beam splitter 1313, so the optical power received from reference arm 104 by detector 1316 (detector C) is equal to the sum of optical power received from reference arm 104 by detector 1314 (detector A) and detector 1315 (detector B); and 4) All detectors have substantially the same responsivity to light intensity;

then, the light on each detector can be processed as follows. The photo-current generated by detector 1314 and detector 1315 can be expressed as:

$$I_A \propto R \cdot \left( \frac{1}{4} P_r + \frac{1}{4} P_s + \frac{1}{2} \cdot \sqrt{P_r \cdot P_s} \cdot \cos(\phi) \right)$$

$$I_B \propto R \cdot \left( \frac{1}{4} P_r + \frac{1}{4} P_s + \frac{1}{2} \cdot \sqrt{P_r \cdot P_s} \cdot \sin(\phi) \right)$$

Here R is the responsivity of photo detectors, $P_r$ is optical power reflected back from reference arm 104, $P_s$ is optical power reflected back from sampling arm 105, and $\phi$ is polarization phase of light from sample arm 105. The photo-current in detector C 1316 can be expressed as:

$$I_C \propto R \cdot \left( \frac{1}{2} P_r + \frac{1}{2} P_s - \frac{1}{2} \cdot \sqrt{P_r \cdot P_s} \cdot \cos(\phi) - \frac{1}{2} \cdot \sqrt{P_r \cdot P_s} \cdot \sin(\phi) \right)$$

The following equation can be utilized:

$$I_u = \frac{1}{2} \cdot (I_A + I_B - I_C) = \frac{1}{2} \cdot R \cdot \sqrt{P_r \cdot P_s} \cdot (\cos(\phi) + \sin(\phi))$$

$$I_v = I_A - I_B = \frac{1}{2} \cdot R \cdot \sqrt{P_r \cdot P_s} \cdot (\cos(\phi) - \sin(\phi))$$

As shown on the above equation, $P_r$ and $P_s$ are also two orthostatic polarization modes. If these two signals are demodulated separately, then the following polarization independent signal of sample power can be obtained:

$$I_u^2 + I_v^2 = \frac{1}{2} \cdot R^2 \cdot P_r \cdot P_s,$$

which is independent of polarization state $\phi$. Note that the expression of $I_u$ and $I_v$ presented in the above equation, which represents the output signal of an optical signal processor 410 coupled to detectors 1314, 1315, and 1316, does not have any DC component, so $I_u$ and $I_v$ are free of any excess intensity noise from light source. That means that sensitivity of the detection and signal processing method discussed above is limited only by shot-noise.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An interferometer, comprising:
   a light source;
   an isolator coupled to the light source;
   polarization dependent optics coupled to the isolator;
   a reference arm connected to the polarization dependent optics;
   a sample arm connected to the polarization dependent optics; and
   one or more optical detectors coupled to the polarization dependent optics,
   wherein the polarization dependent optics couples light into the reference arm and the sample arm, receives reflected light from the reference arm and the sample arm, and provides light to the one or more optical detectors such that a polarization independent optical signal can be formed in an optical signal processing unit coupled to the one or more optical detectors,
   wherein the isolator blocks reflected light from the reference arm and the sample arm from entering the light source,
   wherein the isolator comprises a polarization dependent beam splitter, the polarization dependent beam splitter coupled to receive light from the light source and provide a beam of a first polarization, and
   wherein the polarization dependent optics comprises:
      a Faraday rotator and a wave plate coupled to receive the beam of the first polarization and output the beam of the first polarization;
      a second polarization beam splitter coupled to receive the beam of the first polarization from the Faraday rotator and the wave plate and transmit the beam of the first polarization; and
      a beam splitter coupled to receive the beam of the first polarization from the second polarization beam splitter, couple the beam of the first polarization in the sample arm and the reference arm, receive a reflected beam from the sample arm and the reference arm, and combine the reflected beams from the sample arm and the reference arm into a combined reflected beam,
   wherein, the combined reflected beam is separated into a combined reflected beam of the first polarization and a combined reflected beam of a second polarization by the second polarization beam splitter, the combined reflected beam of the second polarization being coupled to one of the one or more optical detectors, and
   wherein the combined reflected beam of the first polarization is polarization rotated to the second polarization by the Faraday rotator and the wave plate and coupled into another of the one or more optical detectors by the polarization beam splitter.

2. An interferometer, comprising:
   a light source;
   an isolator coupled to the light source;
   polarization dependent optics coupled to the isolator;
   a reference arm connected to the polarization dependent optics;
   a sample arm connected to the polarization dependent optics; and
   one or more optical detectors coupled to the polarization dependent optics,
   wherein the polarization dependent optics couples light into the reference arm and the sample arm, receives reflected light from the reference arm and the sample arm, and provides light to the one or more optical detectors such that a polarization independent optical signal can be formed in an optical signal processing unit coupled to the one or more optical detectors,
   wherein the isolator blocks reflected light from the reference arm and the sample arm from entering the light source,
   wherein the isolator comprises a polarization dependent beam splitter, the polarization dependent beam splitter coupled to receive light from the light source and provide a beam of a first polarization, and
   wherein the polarization dependent optics comprises:
      a Faraday rotator and wave plate coupled to receive the first beam of the first polarization and rotate the polarization to a second polarization;
      a second prism coupled to receive the beam of the second polarization from the Faraday rotator and wave plate;
      a beam splitter coupled to receive the beam of the second polarization from the second prism, couple light into the reference arm and the sample arm, receive a reflected beam from the sample arm the reference arm, and provide a combined reflected beam,
   wherein the combined reflected beam is separated by polarization in the second prism into a first reflected beam of the first polarization and a second reflected beam of the second polarization, wherein the Faraday rotator and wave plate rotates the polarization of the second reflected beam of the second polarization into the first polarization, and wherein the polarization dependent beam splitter couples the second reflected beam into the one or more optical detectors.

3. The interferometer of claim 2, further including a power monitor coupled to the beam splitter.

4. An interferometer, comprising:

a light source;

an isolator coupled to the light source;

polarization dependent optics coupled to the isolator;

a reference arm connected to the polarization dependent optics;

a sample arm connected to the polarization dependent optics; and one or more optical detectors coupled to the polarization dependent optics, wherein the polarization dependent optics couples light into the reference arm and the sample arm, receives reflected light from the reference arm and the sample arm, and provides light to the one or more optical detectors such that a polarization independent optical signal can be formed in an optical signal processing unit coupled to the one or more optical detectors, wherein the isolator blocks reflected light from the reference arm and the sample arm from entering the light source, wherein the isolator comprises a polarization dependent beam splitter, the polarization dependent beam splitter coupled to receive light from the light source and provide a beam of a first polarization, and wherein the polarization dependent optics comprises:

a Faraday rotator and wave plate coupled to receive the first beam of the first polarization and transmit the first beam of the first polarization;

a second prism coupled to receive the first beam of the first polarization from the Faraday rotator and wave plate;

a beam splitter coupled to receive the first beam of the first polarization from the second prism, couple light into the reference arm and the sample arm, receive a reflected beam from the sample arm the reference arm, and provide a combined reflected beam, wherein the combined reflected beam is separated by polarization in the second prism into a first reflected beam of the first polarization and a second reflected beam of the second polarization, wherein the Faraday rotator and wave plate transmits the first reflected beam of the first polarization, and wherein the polarization dependent beam splitter couples the first reflected beam into the one or more optical detectors and wherein the second prism couples the second reflected beam of the second polarization into the one or more detectors.

5. The interferometer of claim 4, further including a power monitor coupled to the beam splitter.

6. An interferometer, comprising:

a light source;

an isolator coupled to the light source;

polarization dependent optics coupled to the isolator;

a reference arm connected to the polarization dependent optics;

a sample arm connected to the polarization dependent optics; and one or more optical detectors coupled to the polarization dependent optics, wherein the polarization dependent optics couples light into the reference arm and the sample arm, receives reflected light from the reference arm and the sample arm, and provides light to the one or more optical detectors such that a polarization independent optical signal can be formed in an optical signal processing unit coupled to the one or more optical detectors, wherein the isolator blocks reflected light from the reference arm and the sample arm from entering the light source, wherein the isolator comprises a circulator coupled to receive light from the light source in a first port, wherein the polarization dependent optics comprises:

a polarization dependent beam splitter coupled to receive light from a second port of the circulator, the polarization dependent beam splitter providing a first beam;

a beam splitter coupled to receive the first beam, to provide light to the sample arm and the reference arm, and receive a reflected beam from the sample arm and the reference arm, wherein a first part of the reflected beam is coupled into the one or more optical detectors by the beam splitter and a second part of the reflected beam is coupled into the polarization dependent beam splitter by the beam splitter, wherein the second part with a first polarization is coupled into the second port of the circulator, the third port of the circulator being coupled to the one or more optical detectors, and wherein the second part with a second polarization is coupled into the one or more optical detectors by the polarization dependent beam splitter.

* * * * *

UNITED STATES PATENT AND TRADEMARK OFFICE
CERTIFICATE OF CORRECTION

PATENT NO. : 7,280,221 B2  Page 1 of 1
APPLICATION NO. : 11/055900
DATED : October 9, 2007
INVENTOR(S) : Jay Wei It is certified that error appears in the above-identified patent and that said Letters Patent is hereby corrected as shown below:

In claim 2, column 18, line 63, "arm the" should read --arm and the--.

In claim 4, column 19, line 45, "arm the" should read --arm and the--.

Signed and Sealed this

First Day of January, 2008

JON W. DUDAS
*Director of the United States Patent and Trademark Office*